United States Patent [19]

Clark et al.

[11] Patent Number: 5,530,004
[45] Date of Patent: Jun. 25, 1996

[54] ANTIMYCOBACTERIAL METHOD

[75] Inventors: Alice M. Clark; Charles D. Hufford, both of Oxford; Shihchih Liu, University, all of Miss.; Babajide O. Oguntimein, Adelphia, Md.; John R. Peterson, Oxford; Jordan K. Zjawiony, University, both of Miss.

[73] Assignee: The University of Mississippi, University, Miss.

[21] Appl. No.: 90,594

[22] Filed: Jul. 12, 1993

Related U.S. Application Data

[62] Division of Ser. No. 715,776, Jun. 14, 1991, Pat. No. 5,227,383.

[51] Int. Cl.⁶ .......................... A61K 31/44; C07D 221/18
[52] U.S. Cl. ................................ 514/284; 546/61
[58] Field of Search .................... 546/61; 514/284

[56] References Cited

PUBLICATIONS

Chemical Abstracts, RN 111326–46–6, 1995.
CA 54: 18527g (Zanker et al, Chem. Ber. 93, 850–60 (1960)).
CA 108: 94363 (Prato, et al., Gazz. Chim. Ital. 1987, 117(5), 325–6 (Eng.)).

*Primary Examiner*—Gary Geist
*Assistant Examiner*—Catherine Kilby Scalzo
*Attorney, Agent, or Firm*—Morgan & Finnegan

[57] ABSTRACT

New analogs of sampangine and cleistopholine, compositions and methods of preparation thereof, method of treating fungal and mycobacterial infections.

1 Claim, No Drawings

ANTIMYCOBACTERIAL METHOD

This is a divisional of application Ser. No. 07/715,776 filed Jun. 14, 1991, now U.S. Pat. No. 5,227,383.

BRIEF DESCRIPTION OF THE INVENTION

This invention is directed to a new analogs of 3-Methoxysampangine, compositions thereof, a method of preparation an a method of providing effective protection against pathological fungal and mycobacterial conditions in mammals particularly those caused by *Candida albicans, Aspergillus fumigatus, Cryptococcus neoformans,* and *Mycobacterium intracellulare* and *Mycobacterium avium intracellulare.*

This application is co-pending with application Ser. No. 07/609,610 NEW COMPOUND AND COMPOSITION USEFUL AS AN ANTIFUNGAL AGENT.

SUMMARY AND BACKGROUND OF THE INVENTION

The need for new, more effective, and less toxic antifungal antibiotics for the treatment of disseminated mycotic and mycobacterial infections is urgent in view of the significant toxicities and failure rates of the currently available systemic antifungal agents. The problem has become particularly relevant in view of the fact that opportunistic disseminated mycoses and atypical mycobacterial infection are common complications of Acquired Immune Deficiency Syndrome (AIDS). The discovery of new antibiotics has in the past successfully relied primarily upon the isolation of such agents from natural sources. The principal advantage of this approach over chemical synthesis or modification of existing agents is the probability of discovering new prototype drugs with quite different chemical structures and, therefore, dissimilar toxidties and cross-resistance with present drug therapies.

The discovery and extraction of an antifungal alkaloid eupolauridine from the stem and root bark of the tree *Cleistopholis patens* (Benth) Engl. and Diels (Annonaceae) and useful against *Candida albicans* is the subject of U.S. Pat. No. 4,965,272. The discovery of eupolauridine from the ethanolic extract of the root bark of the tree which is found throughout West Africa and its possibly remarkable anticandidal properties was reported in the Journal of Natural Products, Vol. 50, No. 5, pp. 961–964, Sept.-Oct. 1987 by Hufford et al. Subsequent to the discovery of eupolauridine in the ethanolic extract and its unexpected antifungal properties, the ethanolic extract was subjected to further examination using different bioassay techniques which resulted in the unexpected discovery of a new compound, 3-Methoxysampangine, and certain analogues thereof which exhibits remarkable antifungal properties against *Canalida albicans, Aspergillus fumigatus,* and *Cryptococcus neoformans* is the subject of co-pending Application Ser. No. 07/609,610. The present invention is concerned with newly discovered analogues of 3-Methoxysampangine, compositions thereof, the method of preparing the novel compounds, and the method of treatment of pathological conditions caused by fungal and mycobacterial organisms comprising administering the compound to mammals in a therapeutically-effective concentration in a non-toxic pharmaceutically-acceptable carrier.

Administration of the compound may be by any of the conventional routes of administration, for example, oral, intramuscular, intravenous, or rectally. In the preferred embodiment, the compound is administered in combination with a pharmaceutically-acceptable carrier which may be solid or liquid, dependent upon choice and route of administration. Examples of acceptable carriers include, but are not limited to, starch, dextrose, sucrose, lactose, gelatin, agar, stearic acid, magnesium stearate, acacia, and similar carriers. Examples of liquids include water, edible oils, e.g. peanut and corn.

When administered in solid form, the compound and diluent carrier may be in the form of tablets, capsules, powders, lozenges, suppositories prepared by any of the well known methods. When given as a liquid preparation, the mixture of active compound and liquid diluent carrier may be in the form of a suspension administered as such. The compound is administered in a non-toxic dosage concentration sufficient to inhibit the growth and/or destroy the *Candida albicans, Aspergillus fumigatus, Cryptococcus neoformans,* and *Mycobacterium intracellulare* organisms. The actual dosage unit will be determined by the well recognized factors as body weight of the patient and/or severity an& type of pathological condition the patient might be suffering with prior to becoming infected with any of the fungal organisms. With these considerations in mind, the dosage unit for a particular patient can be readily determined by the medical practitioner in accordance with the techniques known in the medical arts.

DETAILED DESCRIPTION OF THE INVENTION

The structural formula of 3-Methoxysampangine is as follows:

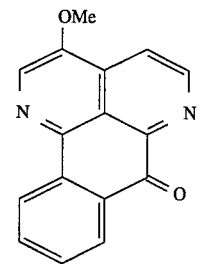

The antifungal and antimycobacterial activity of the novel compounds of the invention was determined by in vitro evaluation against *Candida albicans* NIH B311, *Cryptococcus neoformans* ATCC 32264, *Aspergillus fumigatus* ATCC 26934, and *Mycobacterium intracellulare* ATCC 23068 using the known agar-well diffusion assay techniques with the following modifications.

In the testing of the inventive compounds, *Candida albicans* NIH B311 used to induce experimental disseminated candidiasis was used for the initial qualitative evaluation of anticandidal activity. The organism was grown in Sabouraud-dextrose broth (SDB) for 24 hours at 37°, at which time the cells were harvested by centrifugation at (4°, 2000 rpm, 3 min.). After centrifugation, the cells were washed and suspended in sterile 0.9% saline to give a final concentration of $10^6$ colony forming units (CFU) per ml (adjusted using a hemocytometer). Inocula of *Cryptococcus neoformans* and *Aspergillus fumigatus* were prepared by suspension of the surface growth of stock agar slants in sterile $H_2O$. Culture plates (15×100 mm) for the qualitative assay were prepared from 25 ml of Sabouraud-dextrose agar for *Candida albicans,* and Mycophil™ agar for *Cryptococcus neoformans* and *Aspergillus fumigatus.* Using sterile cotton swabs, the plates were streaked with the suspension of appropriate test organism. Cylindrical plugs were removed from the agar plates by means of sterile cork borer to produce wells with a diameter of approximately 11 mm. To the well was added 100 µl of solution or suspension of an extract, fraction, or pure compound. Crude extracts and fractions were tested at a concentration Of 20 mg/ml, whereas pure compounds were tested at 1 mg/ml. When solvents other than water, ethanol, methanol, dimethylsulfoxide (DMSO), dimethylformamide (DMF), or acetone were required to dissolve extracts or compounds, solvent blanks were included. Antifungal activity was recorded as the width (in mm) of the zone of inhibition, measured from the edge of the agar well to the edge of the zone, following incubation of the plates for 24 hours (37° for *Candida albicans*, 30° for *Aspergillus fumigatus* and 26° for *Cryptococcus neoformans*). The antifungal agents amphotericin B and ketoconazole were included as positive controls in each assay. For qualitative in vitro antimycobacterial evaluation, *Mycobacterium intracellulare* ATCC 23068 is grown in Lowenstein-Jensen (L-J) medium for 48 h at 37°. The remainder of the assay is conducted as described above, except that the culture medium is Mueller-Hinton broth. Rifampin is currently used as a positive control in the antimycobacterial assay.

The method used to determine the minimum inhibitory concentration (MIC) was the twofold serial broth dilution assay in yeast nitrogen broth for *Candida albicans,* Mycophil™ broth for *Cryptococcus neoformans,* and Sabouraud-dextrose broth (SDB) for *Aspergillus fumigatus,* and Mueller-Hinton broth for *Mycobacterium intracellulare.* The inoculum for the MIC determination was prepared as described above for the qualitative evaluation. Using a calibrated sterile wire loop, each tube was inoculated with 10 µl of the suspension. The MIC value was taken as the lowest concentration of compound that inhibited the growth of the test organisms after an appropriate incubation period (37° for 24 hours for *Candida albicans;* 30° for 48 hours for *Aspergillus furnigatus;* 26° for 48 hours for *Cryptococcus neoformans;* 37° for 72 h for *Mycobacterium intracellulare*). The antifungal agent amphotericin B was included as positive control in each antifungal assay and rifampin in the antimycobacterial evaluation. The results of the tests utilizing the new compounds and compositions of the invention demonstrates significant antifungal activity against both yeasts, *Candida albicans* and *Cryptococcus neoformans* and the filamentous fungus, *Aspergillus furnigatus,* and the atypical mycobacterium *Mycobacterium intracellulare.* The test results are set out in Table I. The data in Table I further clearly demonstrates that the new compounds of the invention exhibit in vitro activity against one or more fungal or mycobacterial pathogens at potencies comparable to, and in many cases better than, a current drug of choice, amphotericin B or the antimycobacterial control rifampin.

The compounds of the invention were synthesized according to the inventive method set out in Scheme I. Cleistopholine (3) was obtained in a single step (57% yield) through the hereto Dieis-Alder reaction of 2-bromo-1,4-naphthoquinone (1) with (E)-2-butenal N,N-dimethylhydrazone (2), followed by in situ elimination of dimethylammonium bromide. The condensation of cleistopholine with

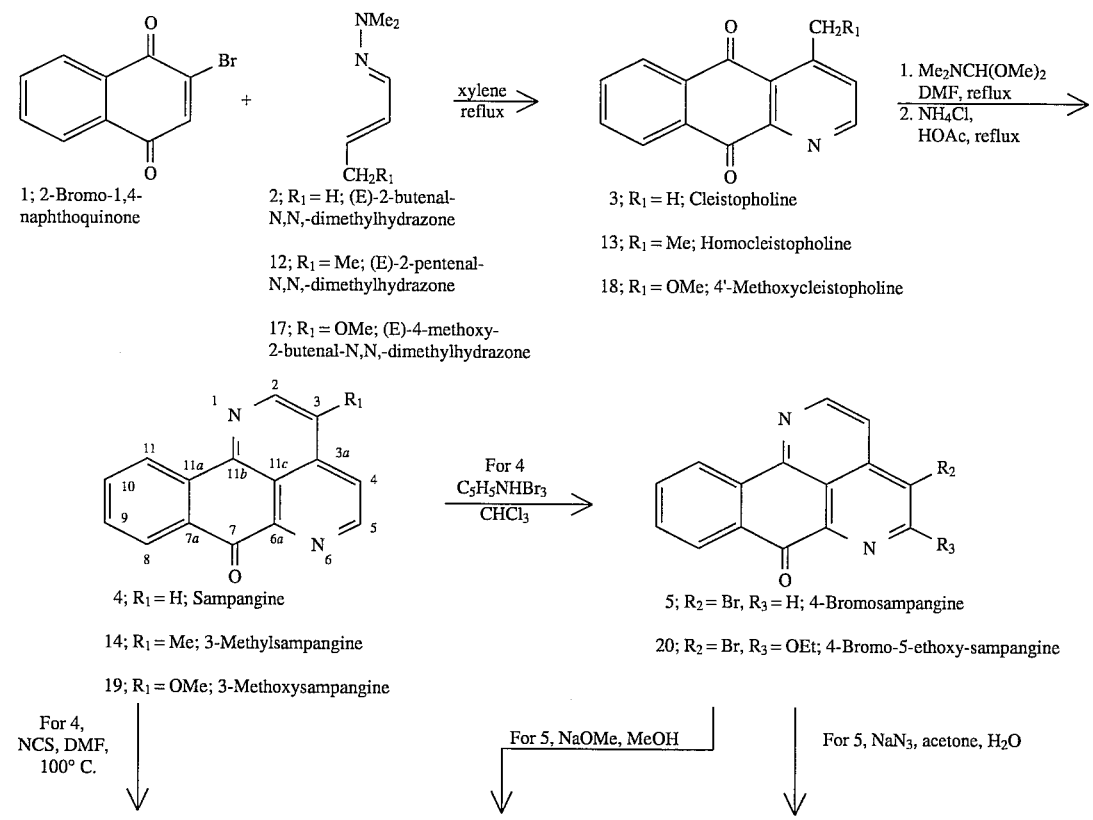

Revised Scheme I

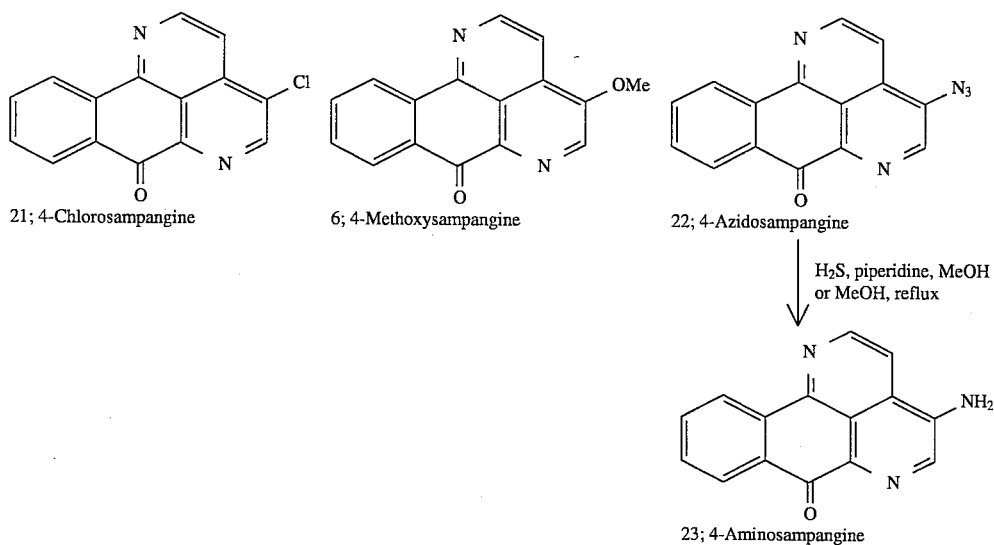

-continued
Revised Scheme I

21; 4-Chlorosampangine

6; 4-Methoxysampangine

22; 4-Azidosampangine

23; 4-Aminosampangine

TABLE I

Additional In Vitro Antifungal and Antimycobacterial Activities

| Compound | Organism[a] | | | |
|---|---|---|---|---|
| | Ca[b] | Cn[c] | Af[d] | Mi[e] |
| Sampangine | 1.56 | 0.78 | 1.56 | 0.78 |
| 4-Bromosampangine | 3.12 | 0.10 | 50 | 3.12 |
| 4-Bromo-5-ethoxy sampangine | NT | 25 | NT | 25 |
| 4-Chlorosampangine | 50 | 0.10 | NT | 3.12 |
| 4-Azidosampangine | 25 | 6.25 | NT | NT |
| 4-Aminosampangine | 100 | 25 | NT | NT |
| 4-Methoxysampangine | 3.12 | 1.56 | NT | 3.12 |
| 3-Methoxysampangine | 1.56 | 0.78 | 0.78 | 1.56 |
| 3-Methylsampangine | 0.39 | 0.39 | 0.78 | 0.39 |
| Benzo[4,5]sampangine | 0.39 | 1.56[f] | 0.39 | 0.39 |
| Cleistopholine | 12.5 | 1.56 | 100 | 12.5 |
| Homocleistopholine | 100 | 3.12 | NT | 12.5 |
| Benzo[2,3]cleistopholine | 25 | 25 | NT | 1.56 |
| Compound 16 | NT | NT | NT | NT |
| Amphotericin B | 0.78 | 0.39 | 0.39 | NT |
| Rifampin | NT | NT | NT | 0.78 |

[a]Activity expressed as minimum inhibitory concentration (MIC) in μg/mL; NT = not tested.
[b]Ca = *Candida albicans* B311 in yeast nitrogen broth.
[c]Cn = *Cryptococcus neoformans* ATCC 32264 in Mycophil ™ broth.
[d]Af = *Aspergillus fumigatus* ATCC 26934 in Sabouraud-dextrose broth.
[e]Mi = *Mycobacterium intracellulare* ATCC 23068 in Mueller-Hinton broth.
[f]Tested in yeast nitrogen broth dimethylformamide dimethyl acetal provided sampangine (4) in 79% yield. Electrophilic bromination of sampangine with pyridinium bromide perbromide or bromine/pyridine complex delivered* 4-bromosampangine (5, 64%), along with a small amount (1%) of 4-bromo-5-ethoxysampangine(20), rather than the anticipated 3-bromo analog. The reaction of N-halosuccinimides with sampanglue likewise afford the 4-halo analogs. For example, the treatment of sampangine with N-chlorosuccinimide in dimethylformamide provided 4-chlorosampangine (21) in 53% yield. Methanolysis of 4-bromosampangine subsequently led to 4-methoxysampangine (6) in 55% yield. The NMR spectral data for sampangine and 4-methoxysampangine are compared with that for 3-methoxysampangine in Tables II and III. These assignments are based on a careful analysis of the $^1$H, attached proton test (APT), correlated spectroscopy (COSY), and short and long range (J=5 and 10 Hz) heterocorrelated (HETCOR) NMR spectra for each compound. The unambiguous C-7 carbonyl resonance allows for a clear recognition of certain key atoms through HETCOR three-bond connections (eg. H-8, C-10, etc.) and thence the remaining atoms by correlation with the other spectra. Consistent with these assignments are significant chemical shift changes for C-4, C-5, C-6a, H-3 and H-5 of 4-methoxysampangine and C-2, C-3, C-11b, H-2 and H-4 of 3-methoxysampangine relative to sampangine.

It was unexpectedly discovered that a modification of the foregoing method for preparing sampangine enabled the preparation of 3-methoxysampangine (19) and 3-methylsampangine (14) heretofore never achieved. The Hetero Diels-Alder reaction of 2-bromo-1,4-naphthoquinone (1) with (E)-4-methoxy-2-butenal N,N-dimethylhydrazone (17) or (E)-2-pentenal N,N-dimethylhydrazone (12) gave 4'-methoxycleistopholine (18) or homocleistopholine (13), respectively, in modest yield. Generation of the sampanglue nucleus (i.e., 3-methoxysampangine (19) and 3-methylsampangine (14)) was accomplished through condensation of the corresponding cleistopholine with dimethylformamide dimethylacetal. For the 3-methylsampangine reaction, at least two additional compounds, 4'-oxohomocleistopholine (15) and dimer 16, were produced in significant quantities. The exact yields for 15 and 16 remain undetermined due to difficulty in isolation. Chromatography of the reaction product gave fractions consisting of recovered homocleistopholine (11%), 3-methylsampangine (6%), and a fraction consisting of compounds 14–16. Recrystallization of the latter fraction from ethyl acetate followed by manual separation of the crystal types gave pure 15 and 16; 3-methylsampangine crystallized as long yellow needles, 4'-oxohomocleistopholine (6%, 15) as nearly perfect golden octahedra, and dimer 16 (6%) as rectangular yellow plates.

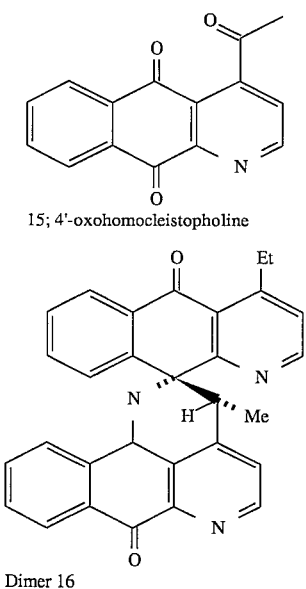

15; 4'-oxohomocleistopholine

Dimer 16

The facility with which the nucleophilic substitution of bromo for methoxy occurred in the case of 4-bromosampangine led to the use of other nucleophiles in this reaction. Indeed, the photolablie 4-azidosampangine (22) could be isolated in 80% yield by workup and column chromatography in a dark room. Thermal decomposition of 4-azidosampangine in turn provided the highly fluorescent 4-aminosampangine (23). This dark red crystalline analog was also obtained by reduction of 4-azidosampangine with hydrogen sulfide, or more directly by substitution of bromide for azide and in situ reduction with hydrogen sulfide in a single pot reaction. The reaction of 4-bromosampangine with potassium amide also provided 4-aminosampangine; however, the yield the product was substantially lower than that by the above methods.

EXAMPLE I

Preparation of 2-Bromo-1,4-naphthoquinone (1). A 3-L, three-necked, round-bottomed flask fitted with a mechanical stirrer, a 500-mL addition funnel and a thermometer, was charged with glacial acetic acid (500 mL), water (1000 mL) and N-bromosuccinimide (71.2 g, 0.40 mol). The mixture was warmed to 45° C. during which time a yellow solution was obtained. An acetic acid (500 mL) solution of 1-naphthol (14.4 g, 0.10 mol) was then added dropwise over a period of 75 min so as to give a red solution, the latter of which was stirred an additional 30 min at 45° C. before cooling to room temperature. The resulting mixture was diluted with water (1500 mL) and extracted with rhethylene chloride (6×400 mL). The combined organic extracts were in turn washed with water (4×400 mL) and saturated sodium bicarbonate solution (4×300 mL). Rotary evaporation of the solvent following drying over magnesium sulfate yielded a yellow solid that was recrystallized from 95% ethanol to yield pure 2-Bromo-1,4-naphthoquinone (18.50 g, 78%); mp 130.5°–132° C. (lit. mp 131°–132° C.). IR(KBr) 3050, 1675, 1655, 1585, 1570, 1330, 1310, 1295, 1270, 1245, 1220, 1120, 1060, 910, 890, 820, 790, 775, 670, 665 cm$^{-1}$; $^1$H NMR (CDCl$_3$) δ8.21–8.14 (m, 1 H), 8.11–8.05 (m, 1 H), 7.80–7.73 (m, 2 H), 7.52 (s, 1 H); $^{13}$C NMR (CDCl$_3$) 182.4 (0), 177.8 (0), 140.3 (1), 140.1 (0), 134.4 (1), 134.1 (1), 131.7 (0), 130.9 (1), 127.8 (1), 126.9 (1) ppm.

EXAMPLE II

Preparation of (E)-2-Butenal N,N-Dimethylhydrazone (2). A 250-mL, round-bottomed flask equipped with a 60-mL addition funnel was charged with crotonaldehyde (74.7 mL, 0.90 mol) and cooled in an ice-water bath. 1,1-Dimethylhydrazine (75.3 mL, 0.99 mol) was then added dropwise to the cold aldehyde over a period of 15 min. The layers were separated after allowing the reaction to stir at ambient temperature for 45 min. The organic layer was dried over calcium chloride, decanted, and distilled through a Vigreaux column. Collection of the fraction boiling at 53°–58° C., 15–18 mm Hg (water aspirator) gave 58.8 g (58%) of pure (E) - 2-Butenal N,N-dimethylhydrazone. $^1$H NMR (CDCl$_3$) δ6.98 (d, J=8.9 Hz, 1 H), 6.18 (ddq, J=15.5, 8.9, 1.7 Hz, 1 H), 5.78 (dq, J=15.5, 6.8 Hz, 1 H), 2.78 (s, 6 H), 1.78 (dd, J=6.8, 1.7 Hz, 3 H).

EXAMPLE III

Preparation of Cleistopholine (4). (E)-2-Butenal N,N-dimethylhydrazone, (3.70 g, 0.033 mol) in dry xylene (10 mL, Fisher) was added to a xylene solution (50 mL) of 2-bromo- 1,4-naphthoquinone, (6.00 g, 0.025 mol) in a 200-mL, round-bottomed flask fitted with a condensor. The dark mixture was then heated at reflux for 6 h under a nitrogen atmosphere before decanting the solution into a 500-mL separatory funnel. The solids coating the wall of the flask were washed thoroughly with ethyl acetate (6×25 mL) and these washings added to the separatory funnel. The combined organic solutions were extracted with 2N sulfuric acid solution (1×100 mL followed by 2×75 mL). The acid layers were then combined, chilled in ice, and made basic (~pH 10 test paper) with sodium hydroxide before extracting with ethyl acetate (4×100 mL). The latter organic layers were dried over potassium carbonate and concentrated to dryness on a rotary evaporator. This material was applied to a 4×70 cm column of Silica gel (Merck 230–400 mesh) and the product Muted with ethyl acetate. Concentration of the appropriate column fractions yielded pure cleistopholine (3.20 g, 57%); mp 202°–204° C. (lit. mp 198°–201° C.). IR (KBr) 1680, 1660, 1590, 1300, 980, 720 cm$^{-1}$; $^1$H NMR (CDCl$_3$) δ8.86 (d, J=4.9 Hz, 1 H), 8.34–8.30 (m, 1 H), 8.24–8.19 (m, 1 H), 7.82–7.76 (m, 2 H), 7.47 (dd, J=4.9, 0.7 Hz, 1 H), 2.88 (br s, 3 H); $^{13}$C NMR (CDCl$_3$) 184.7 (0), 181.9 (0), 153.4 (1), 151.5 (0), 150.0 (0), 134.5 (1), 134.1 (1), 133.8 (0), 132.5 (0), 131.2 (1), 129.1 (0), 127.3 (1), 127.1 (1), 2.28 (3) ppm.

EXAMPLE IV

Preparation of Sampanglue (4). Dimethylformamide dimethyl acetal (1.50 mL, 11.34 mmol, Aldrich) was added to a solution of cleistopholine, (1.95 g, 8.73 mmol) in dimethylformamide (5 mL). The mixture was then heated for 30 min by submerging the reaction vessel into an oil bath preheated to 120° C. At this point, ammonium chloride (4.5 g) and glacial acetic acid (15 mL) were added to the reaction and the heating (120° C.) continued for an additional 30 min. After allowing to cool, the reaction was poured onto water (200 mL) and partitioned with methylene chloride (5×100 mL). The combined organic phases were washed with saturated sodium bicarbonate solution (3×100 mL), water (3×100 mL), dried over potassium carbonate, and concentrated to dryness. The residual dark brown solids were chromatographed on silica gel (4×70 cm column, Merck 230–400 mesh) while eluting with ethyl acetate. Concentration of the appropriate column fractions provided pure sampangine (1.60 g, 79%), mp 220–222 (lit. mp 216°–218° C.). IR 1670, 1615, 1590, 1400, 1380, 1320, 1275, 1225, 760, 725 cm$^{-1}$; $^1$H and $^{13}$C NMR.

EXAMPLE V

Preparation of 4-Bromosampangine (5). A mixture of pyridinium bromide perbromide (390 mg, 1.2 mmol) and sampangine, (232 mg, 1.0 mmol) in chloroform (12 mL) was heated at reflux for 15 h. Saturated sodium bicarbonate solution (100 mL) was added to the cooled reaction and the mixture stirred vigorously for 30 min. The two layers were separated and the aqueous phase extracted with chloroform (2×30 mL). The combined organic layers were dried over potassium carbonate and concentrated to dryness. The residual solid was applied to a 2×40 cm column of silica gel (Merck 230–400 mesh) and the pure product (200 mg, 64%) eluted with chloroform, mp 180° C. dec. IR (KBr) 1670, 1590, 1400, 1320, 1310, 1275, 1230, 980, 790, 755, 720 cm$^{-1}$; $^1$H NMR (CDCl$_3$) δ9.28 (s, 1 H), 8.99 (d, J=5.9 Hz, 1 H), 8.85 (dd, J=7.9, 1.4 Hz, 1 H), 8.46 (dd, J=7.9, 1.4 Hz, 1 H), 7.96 (d, J=5.9 Hz, 1 H), 7.86 (ddd, J=7.7, 7.9, 1.4 Hz, 1 H), 7.72 (ddd, J=7.9, 7.9, 1.4 Hz, 1 H); $^{13}$C NMR (CDCl$_3$) 181.6 (0), 151.7 (0), 150.2 (1), 148.6 (1), 146.7 (0), 138.6 (0), 135.1 (0), 135.0 (1), 132.3 (0)), 131.8 (1), 128.7 (1), 125.8 (1), 123.7 (0), 120.5 (0), 118.3 (1) ppm; HR MS calc. for C$_{15}$H$_7$BrN$_2$O 309.9741, found 309.9747.

EXAMPLE VI

Electrophilic Bromination of Sampangine: Preparation of 4-Bromo-7H-naphtho[1,2,3-ij] [2,7]naphthyridin-7-one [4-Bromosampangine, 5] and 4-Bromo- 5-ethoxy-7H-naphtho[1,2,3-ij] [2,7]naphthyridin-7-one[4-Bromo-5-ethoxysampangine, 20]. A mixture of pyridinium bromide perbromide (4.80 g, 15.0 mmol) and sampangine (2.32 g, 10.0 mmol) in CHCl$_3$ (100 mL) was heated at reflux for 24 h. After cooling, the mixture was poured into a separatory funnel and washed with saturated aqueous NaHCO$_3$ Solution (2×250 mL). The organic layer was dried (K$_2$CO$_3$) and concentrated to dryness. The residual solids were subjected to flash silica gel chromatography while eluting with CHCl$_3$ to give pure 4-bromosampangine (5) (2.00 g, 64%) and 4-bromo-5-ethoxysampangine (20) (0.05 g, 1%). An analytical sample of 20 was obtained by crystallization from CHCl$_3$. Compound 5: mp 244°–246 ° C.; IR (KBr) 1670, 1590, 1400, 1320, 1310, 1275, 1230, 980, 790, 755, 720 cm$^{-1}$; $^1$H NMR (CDCl$_3$) δ7.72 (ddd, 1 H, J=7.9, 7.9, 1.4 Hz), 7.86 (ddd, 1 H, J=7.9, 7.9, 1.4 Hz), 7.96 (d, 1 H, J=5.9 Hz), 8.46 (dd, 1 H, J=7.9, 1.4 Hz), 8.85 (dd, 1 H, J=7.9, 1.4 Hz), 8.99 (d, 1 H, J=5.9 Hz), 9.28 (s, 1H); $^{13}$C NMR (CDCl$_3$) 118.3 (1), 120.5 (0), 123.7 (0), 125.8 (1), 128.7 (1), 131.8 (1), 132.3 (0), 135.0 (1), 135.1 (0), 138.6 (0), 146.7 (0), 148.6 (1), 150.2 (1), 151.7 (0), 181.6 (0) ppm; Anal. (exact mass, HREIMS) calcd for C$_{15}$H$_7$BrN$_2$O m/e 309.9741, found 309.9747; Anal. calcd for C$_{15}$H$_7$BrN$_2$O: C 57.90, H 2.27, N 9.00; found C 57.70, H 2.27, N 9.26. Compound 20: mp 200°–201° C.; IR (KBr) 1670, 1592, 1570, 1430, 1382, 1365, 1330, 1270, 1212, 1080, 1070, 1042, 980, 845, 762, 755, 720, 710, 635 cm$^{-1}$; $^1$H NMR (CDCl$_3$) δ1.56 (t, 3 H, J=7.1 Hz), 4.79 (q, 2 H, J=7.1 Hz), 7.67 (ddd, 1 H, J=7.3, 7.3, 1.4 Hz), 7.79 (ddd, 1 H, J=7.3, 7.3, 1.4, Hz), 7.82 (d, 1 H, J=6.1 Hz), 8.36 (dd, 1 H, J=7.3, 1.4 Hz), 8.72 (d, 1 H, J=6.1 Hz), 8.75 (dd, 1 H, J=7.3, 1.4 Hz); $^{13}$C NMR (CDCl$_3$) 14.6 (3), 64.7 (2), 107.4 (0), 117.5 (0), 117.8 (1), 125.5 (1), 128.2 (1), 131.4 (0), 132.2 (0), 134.5 (1), 135.0 (0), 140.9 (0), 144.6 (0), 147.2 (1), 151.7 (0), 159.9 (0), 181.4 (0) ppm; Anal. calcd for C$_{17}$H$_{11}$BrN$_2$O: C 57.48, H 3.12, N 7.88; found C 57.09, H 3.37, N 7.75.

EXAMPLE VII

Preparation of 4-Methoxysampangine (6). A dry methanol (6 mL) solution of sodium methoxide (80 mg, 1.48 mmol) and 4-bromosampangine, (80 mg, 0.26 mmol) was heated to reflux for 20 h. The cooled solution was transferred to a separatory funnel, diluted with chloroform (50 mL), and washed with water (2×60 mL). The chloroform layer was subsequently dried over potassium carbonate and concentrated to dryness. TLC analysis of the residue (silica gel, ethyl acetate eluant) revealed only one spot (R$_f$=0.15) that was substantially more polar than 4-methoxysampangine. Chromatography of this residue on silica gel (1×25 cm column, Merck 230–400 mesh) while eluting with ethyl acetate-methanol (4:1) provided pure 4-methoxysampangine (37 mg, 55%), mp 258° C. dec. IR (KBr) 1670, 1595, 1570, 1500, 1405, 1375, 1320, 1295, 1240, 1100, 1040, 1030, 985, 920, 790, 720, 615 cm$^{-1}$; $^1$H and $^{13}$C NMR.

EXAMPLE VIII

Preparation of Benzo[4,5]sampangine (9). As illustrated in Scheme II, a suspension of 4.47 g (0.03 mol) of 1,4-naphthoquinone (7) in 600 ml of absolute ethanol, containing 3.37 g (0.03 mol) of [1] 2'-aminoacetophenone (8) and 1.66 g (0.003 mol) of cerium trichloride heptahydrate was warmed to dissolve, then allowed to stand at room temperature and a steady current of air was continuously blown into

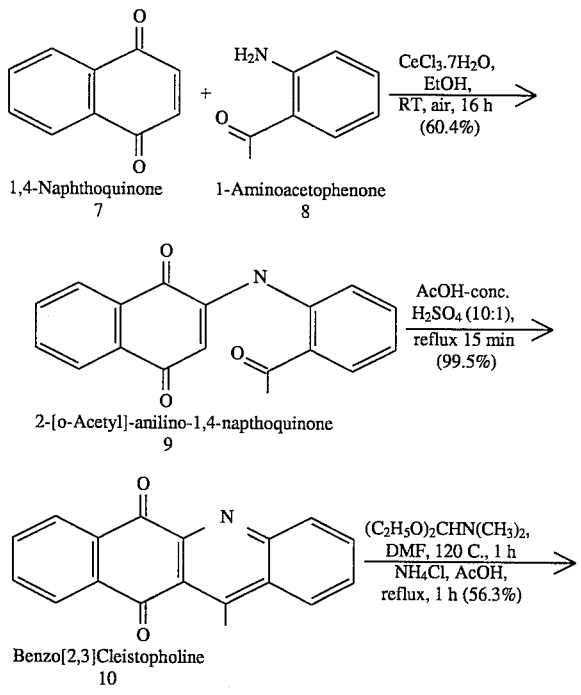

Scheme II 1,4-Naphthoquinone 7

1-Aminoacetophenone 8

2-[o-Acetyl]-anilino-1,4-napthoquinone 9

Benzo[2,3]Cleistopholine 10

-continued
Scheme II

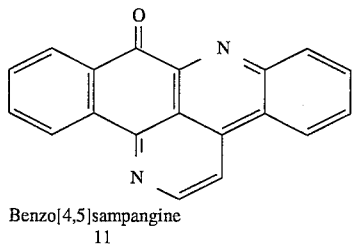

Benzo[4,5]sampangine
11 the reaction mixture for 24 h. A red precipitate was formed and collected by filtration, then washed with a small amount of absolute ethanol. The filtrate was subjected to the above procedure twice, and a total of 7.26 g (60.4%) of 2-[o-acetyl]-anilino-1,4-naphthoquinone (9) was obtained as red needles, mp. 177°–179° C. ElMS m/z 291 (M+), $^1$H-nmr, δ(CDCl$_3$) 2.66 (3H, s), 6.99 (1H, s) 7.06 (1H, d, J=9.0Hz), 7.14 (1H, ddd, J=6.0, 6.0, 1.0Hz), 7.55 (1H, ddd, J=9.0, 6.0, 1.0Hz), 7.65 (1H, ddd, J=8.0, 8.0, 1.5Hz), 7.73(1H, ddd, J=8.0,8.0,1.5Hz), 7.93 (1H, dd, J=6.0, 1.0Hz), 8.05 (1H, dd, J=9.0, 1.0Hz), 8.13 (1H, dd, J=9.0, 1.0Hz).

To a cold, stirred suspension of 4 g (15.7 m mols) of 2-[o-acetyl]-anilino-1,4-naphthoquinone (9)in 13.2 mL of glacial acetic acid was slowly added 13.2 ml of concentrated H$_2$SO$_4$. The reaction mixture was then gently refluxed for 15 min., cooled, and poured into 2 liters of ice-H$_2$O. The yellow precipitate was collected and washed with a small amount of ice cold H$_2$O to give 3.23 g (99.5%) of dirty greenish yellow fine needles of Benzo[2,3]cleistopholine (10) top. 237°–239° (d). EIMS M/z 273(M+), IRσ max(KBr) 1680, 1655, 1590, 1495, 1375, 1260, 1080, 943, 770, 720 cm$^{-1}$. $^1$H-nmr, δ(CDCl$_3$) 3.22(3H, s, CH$_3$-13), 7.69(1H, ddd, J=6.7, 6.7, 1.3Hz), 7.70(1H, m),7.78(1H, m), 7.84(1H, ddd, J=6.7, 6.7, 1.3Hz), 8.25(1H, dd, J=6.0, 2.5Hz), 8.29 (1H, brd, J=6.7Hz), 8.34(1H, dd, J=6.0, 2.5Hz), 8.39(1H, brd, J=6.7Hz).

A suspension of 2.38 g (8.73 mmol) of Benzo[2,3]deistopholine in 3 ml of DMF and 1.67 g of dimethyl formamide-diethylacetal was stirred under N$_2$ and heated at 120° C. for 1 h. The reaction mixture was cooled and 15 ml of gladal acetic acid and 4.5 g of NH$_4$Cl was added carefully and the reaction mixture was refluxed for another hour. Water (300 ml) was added to the reaction mixture, followed by extraction with CH$_2$Cl$_2$ (150 ml×4). The total organic layer was washed with 150 ml of saturated NaHCO$_3$ solution, then with 150 ml of H$_2$O, and dried over anhydrous K$_2$CO$_3$. After removal of solvent, the resulting residue was chromatographed over silica gel (400 g) and eluted with ethyl acetate to give 1.824 (56.3%) of Benzo[4,5]sampangine (11), as bright yellow needles, top. 260°–262° C. ElMS m/z 282(M+), IRυ 3 max(KBr) 1680, 1590, 442, 1390, 1300, 1262, 1060, 950, 767, 740 cm$^{-1}$. $^1$H and $^{13}$C NMR (see Table II).

EXAMPLE IX

Preparation of trans-2-Pentenal N,N-Dimethylhydrazone (12). N,N-Dimethylhydrazine (42.0 mL 0.55 mol) was added dropwise to trans-2-pentenal (42.06 g, 0.50 mol) at such a rate that the reaction temperature could be maintained at about 0° C. The mixture was then stirred for 1 h at ambient temperature, and the organic phase separated and dried (K$_2$CO$_3$). Distillation (bp 84°–86° C., 25 mm Hg; lit bp 60° C., 15 mm Hg) through a 10 cm Vigreaux column gave trans-2-pentenal N,N-dimethylhydrazone (12) (51.3 g, 81%): n$^{20}$ 1.5104; IR (neat) 2960, 2870, 2850, 2820, 2780, 1565, 1470, 1460, 1445, 1265, 1135, 1030, 970 cm$^{-1}$; $^1$H NMR (CDCl$_3$) δ0.98 (t, 3 H, J=7.4 Hz), 2.16–2.05 (m, 2 H), 2.76 (s, 6 H), 5.82 (dt, 1 H, J=15.6, 6.3 Hz), 6.14 (dd, 1 H, J=15.6, 8.8 Hz) 6.97 (d, 1 H, J=8.8 Hz).

EXAMPLE X

Preparation of 4-Ethylbenzo[g]quinoline-5,10-dione [Homocleistopholine, 13]. A solution of trans-2-pentenal N,N-dimethylhydrazone (49.15 g, 0.39 mol) in xylene (100 mL) was quickly added to a xylene (600 mL) solution of 2-bromo-1,4-naphthoquinone (71.12 g, 0.30 mol) and the dark reaction heated at reflux for 6 h. Workup followed the procedure described above for cleistopholine. Chromatography provided pure homocleistopholine (13) (10.90 g, 14%). An analytical sample was obtained by crystallization from EtOAc: mp 157°–158° C.; IR (KBr) 1680, 1665, 1590, 1575, 1450, 1340, 1300, 1280, 1260, 1225, 1200, 1000, 955, 870, 850, 800, 790, 730 cm$^{-1}$; $^1$H NMR (CDCl$_3$) δ1.29 (t, 3 H, J=7.4 Hz), 3.28 (q, 2 H, J=7.4 Hz), 7.48 (d, 1 H, J=5.0 Hz), 7.71–7.78 (m, 2 H), 8.14–8.18 (m, 1 H), 8.25–8.28 (m, 1 H), 8.87 (d, 1 H, J=5.0 Hz); $^{13}$C NMR (CDCl$_3$) 14.1 (3), 28.0 (2), 127.1 (1), 127.2 (1), 128.5 (0), 129.3 (1), 132.4 (0), 133.9 (0), 134.0 (1), 134.5 (1), 150.2 (0), 153.6 (1), 157.2 (0), 181.8 (0),

TABLE II $^1$H AND $^{13}$C NMR DATA FOR BENZO[4,5]SAMPANGINE

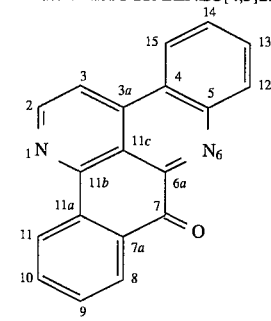

| Position | $^1$H NMR | $^{13}$C NMR |
|---|---|---|
| 2 | 8.97(d, J=5.7Hz, 1H) | 148.9 (1) |
| 3 | 8.30(d, J=5.7Hz, 1H) | 115.5 (1) |
| 3a | — | 137.8 (0) |
| 4 | — | 123.5 (0) |
| 5 | — | 145.8 (0) |
| 6a | — | 146.0 (0) |
| 7 | — | 182.2 (0) |
| 7a | — | 132.5 (0) |
| 8 | 8.44(dd, J=7.8, 1.0Hz, 1H) | 128.7 (1) |
| 9 | 7.66(ddd, J=7.8, 7.4, 1.0Hz, 1H) | 131.2 (1) |
| 10 | 7.80(ddd, J=7.8, 7.4, 1.0Hz, 1H) | 134.9 (1) |
| 11 | 8.79(dd, J=7.8, 1.0Hz, 1H) | 125.8 (1) |
| 11a | — | 136.1 (0) |
| 11b | — | 150.5 (0) |
| 11c | — | 117.0 (0) |
| 12 | 8.55(dd, J=7.1, 1.4Hz, 1H) | 133.1 (1) |
| 13 | 7.93(ddd, J=7.1, 7.0, 1.4Hz, 1H) | 131.6 (1) |
| 14 | 7.84(ddd, J=7.1, 7.0, 1.4Hz, 1H) | 130.3 (1) |
| 15 | 8.55(dd, J=7.1, 1.4Hz, 1H) | 122.9 (1) |

184.5 (0) ppm; Anal. calcd for C$_{15}$H$_{11}$NO$_2$: C 75.94, H 4.67, N 5.90; found C 75.85, H 4.68, N 5.91.

EXAMPLE XI

Preparation of 3-Methyl-7H-naphtho[1,2,3-ij][2,7]naphthyridin-7-one [3-Methylsampangine, 14]; 4-[Ethanone] benzo[g]quinoline-5,10-dione [4'-Oxohomocleistopholine, 15]; and 2,3-Dihydro-4'-ethyl-3α-methylspiro[7H-naphtho[1,2,3-ij][2,7]naphthyridin-7-one-2α,10'-benzo[g]quinoline-5-one], 16. The general procedure outlined above for sampangine was followed beginning with homocleistopholine (7.12 g, 30.0 mmol). Evaporation of the $CH_2Cl_2$ extract provided a product that was a complex mixture by TLC analysis. Flash silica gel chromatography of this material while eluting with $CHCl_3$/EtOAc (9:1) gave fractions consisting of recovered homocleistopholine (0.75 g, 11%), 3-methylsampangine (14) (0.45 g, 6%), and a mixture of 14–16. The latter mixture was separated by crystallization from EtOAc and manual sorting of the crystal types; 3-methylsampangine (14) crystallized as long yellow needles, 4'-oxohomocleistopholine (15) as nearly perfect golden octahedra (0.45 g, 6%) and compound 16 as rectangular yellow plates (0.41 g, 6%). Yields for 15 and 16 represent minimal quantities present as actually isolated by this procedure. 3-Methylsampangine (14): 219°–220° C.; IR (KBr) 1665, 1590, 1570, 1370, 1310, 1285, 1260, 1230, 960, 910, 860, 795, 760, 725 $cm^{-1}$; $^1$H NMR ($CDCl_3$) δ2.65 (s, 3 H), 7.62 (ddd, 1 H, J=7.8, 7.8, 1.3 Hz), 7.76 (ddd, 1 H, J=7.8, 7.8, 1.3 Hz) 7.93 (d, 1 H, J=5.6 Hz) 8.38 (dd, 1 H, J=7.8, 1.3 Hz), 8.56 (br s, 1 H), 8.65 (dd, 1 H, J=7.8, 1.3 Hz), 9.08 (d, 1 H, J=5.6 Hz); $^{13}$C NMR ($CDCl_3$) 15.3 (3), 119.0 (0) 120.5 (1), 124.9 (1), 127.2 (0), 128.3 (1), 130.8 (1), 131.9 (0), 134.5 (1), 135.6 (0), 138.4 (0), 146.8 (1), 148.0 (0), 148.2 (1), 149.1 (0), 182.0 (0) ppm; Anal. calcd for $C_{16}H_{10}N_2O$: C 78.04, H 4.09, N 11.38; found C 78.34, H 4.09, N 11.04. 4'-Oxohomocleistopholine (15): mp 208°–210° C.; IR (KBr) 1700, 1675, 1665, 1580, 1465, 1450, 1350, 1335, 1305, 1270, 1255, 1240, 1200, 1120, 1090, 990, 980, 960, 860, 803, 730, 610 $cm^{-1}$; $^1$H NMR ($CDCl_3$) δ2.61 (s, 3 H), 7.45 (d, 1 H, J=4.7 Hz), 7.81–7.91 (m, 2 H), 8.22–8.26 (m, 1 H), 8.38–8.42 (m, 1 H), 9.14 (d, 1 H, J=4.7 Hz); $^{13}$C NMR ($CDCl_3$) 30.4 (3), 123.7 (1), 126.9 (0), 127.5 (1), 128.1 (1), 132.3 (0), 132.9 (0), 134.9 (1), 135.2 (1), 149.3 (0), 151.5 (0), 155.3 (1), 180.7 (0), 182.7 (0), 202.0 (0) ppm; Anal. calcd for $C_{15}H_9NO_3$; C 71.71, H 3.61, N 5.57; found C 71.64, H 3.70, N 5.60. Compound 16: mp 273°–274° C.; IR (KBr) 2980, 1665, 1620, 1590, 1570, 1550, 1455, 1310, 1280, 1240, 1200, 1160, 1030, 965, 930, 855, 790, 780, 760, 722, 710, 695 $cm^{-1}$; $^1$H NMR ($CDCl_3$) δ0.90 (d, 3 H, J=7.0 Hz), 1.26 (t, 3 H, J=7.4 Hz), 3.18–3.32 (m, 2 H), 3.61 (dq, 1 H, J=1.3, 7.0 Hz), 7.08 (d, 1 H, J=4.9 Hz), 7.22 (dd, 1 H, J=4.8, 1.3 Hz), 7.60 (ddd, 1 H, J=7.8, 5.8, 3.0 Hz), 7.68–7.78 (m, 4 H), 8.07 (d, 1 H, J=4.9 Hz), 8.29 (dd, 1 H, J=7.8, 1.0 Hz), 8.46–8.50 (m, 2 H), 8.87 (d, 1 H, J=4.8 Hz); $^{13}$C NMR ($CDCl_3$) 11.9 (3), 14.5 (3), 28.1 (2), 42.8 (1), 68.0 (0), 123.1 (1), 124.1 (0), 125.3 (1), 125.5 (1), 125.7 (0), 126.4 (1), 127.6 (1), 128.2 (1), 128.3 (1), 131.6 (1), 132.6 (0), 132.8 (0), 133.7 (1), 133.8 (1), 134.9 (0), 143.3 (0), 146.3 (0), 147.8 (0), 151.4 (1), 153.5 (0), 156.3 (0), 156.9 (0), 157.0 (0), 182.8 (0), 186.0 (0) ppm; Anal. calcd for $C_{30}H_{21}N_3O_2 \cdot \frac{1}{2}C_4H_8O_2$: C 76.93, H 5.04, N 8.41; found C 76.85, H 4.69, N 8.46.

EXAMPLE XII

Preparation of(E)-4-Methoxy-2-butenal N,N-Dimethylhydrazone (17). A solution of (Z)-2-buten-1,4-diol (88.11 g, 1.00 mol), sodium hydroxide (55.99 g, 1.40 mol) and $H_2O$ (230 mL) was heated to 70° C. before adding dimethyl sulfate (53.9 mL, 0.57 mol) dropwise. The reaction was then stirred for 2 h at 80° C. before continuously extracting the product with $Et_2O$ in a 1-L extraction apparatus for 26 h. The ether extract was dried ($MgSO_4$) and concentrated by rotary evaporation. Distillation of the product through a 10 cm Vigreaux column gave two fractions; the first fraction (bp 28°–34° C., 25 mm Hg) was identified as (Z)-1,4-dimethoxy-2-butene (13.70 g, 11%) and the higher boiling fraction (bp 92°–100° C., 25 mm Hg) as (Z)-4-methoxy-2-buten-1-ol (38.42 g, 66%).

To a suspension of pyridinium chlorochromate (63.3 g, 0.29 tool) in $CH_2Cl_2$ (500 mL) was added a $CH_2Cl_2$ (80 mL) solution of (Z)-4-methoxy-2-buten-1-ol (28.0 g, 0.27 mol). The reaction immediately darkened and evolved heat. After stirring for 2.5 h at ambient temperature, the mixture was diluted with $Et_2O$ (2000 mL) and filtered through a bed of Florasil. The residual solids in the flask were washed well with $Et_2O$ and the washes passed through the Florasil bed. The organic filtrate was concentrated to an oil and this oil distilled (bp 66°–68° C., 20 mm Hg) with a short path still to give (E)-4-methoxy-2-butenal (14.30 g, 52%). The colorless product turns light yellow shortly after distillation but can be stored overnight in a –20° C. freezer before use: IR (neat) 2990, 2920, 2820, 2720, 1690, 1640, 1450, 1195, 1115, 1035, 970 $cm^{-1}$; $^1$H NMR ($CDCl_3$) δ3.36 (s, 3 H), 4.15 (dd, 2 H, J=4.2, 2.0 Hz), 6.27 (ddt, 1 H, J=15.8, 8.0, 2.0 Hz), 6.78 (dt, 1 H, J=15.8, 4.2 Hz), 9.52 (d, 1 H, J=8.0 Hz); Anal. calcd for $C_5H_8O_2$; C 59.99, H 8.05; found C 59.91, H 8.12.

N,N-Dimethylhydrazine (10.90 mL, 0.14 mol) was added dropwise over 15 min to (E)-4-methoxy- 2-butenal (13.06 g, 0.13 mol) while cooling the reaction with an ice bath. The bath was then removed and the mixture stirred for 1.5 h at ambient temperature. Calcium chloride (20 g) was added to the reaction, let set for 15 min, and the product decanted. Distillation (bp 102°–110 ° C., 25 mm Hg) of the oil through a 10 cm Vigreaux column provided pure (E)-4-methoxy-2-butenal N,N-dimethylhydrazone (17) (14.45 g, 78%): IR (neat) 2850, 2820, 1560, 1465, 1445, 1375, 1270, 1120, 1030, 970 $cm^{-1}$; $^1$H NMR ($CDCl_3$) δ 2.80 (s, 6 H), 3.26 (s, 3 H), 3.93 (dd, 2 H, J=6.2, 1.2 Hz), 5.74 (dr, 1 H, J=15.8, 6.2 Hz), 6.31 (ddt, 1 H, J=15.8, 8.9, 1.2 Hz), 6.92 (d, 1 H, J=8.9 Hz); Anal. calcd for $C_7H_{14}N_2O$: C 59.05, H 10.07, N 19.52; found C 59.13, H 9.92, N 19.70.

EXAMPLE XIII

Preparation of 4-[Methoxymethyl]benzo[g]quinoline-5,10-dione [4'-methoxycleistopholine, 18]. The general procedure described above for cleistopholine was followed while beginning with (E)-4-methoxy-2-butenal N,N-dimethylhydrazone (12.25 g, 86.0 mmol) and 2-bromo-1,4-naphthoquinone (15.71 g, 66.0 mmol) in xylene (160 mL). Flash silica chromatography of the brown product obtained upon workup and elution with EtOAc/petroleum ether (7:3) provided 4'-methoxycleistopholine (18) (1.96 g, 12%). An analytical sample was prepared by crystallization from EtOAc: $^1$H NMR ($CDCl_3$) δ3.60 (s, 3 H), 5.12 (s, 2 H), 7.67–7.93 (m, 2 H), 8.00–8.50 (m, 2 H), 8.67 (dd, 1 H, J=8.1, 2.0 Hz), 9.1 (dd, 1 H, J=8.1, 2.0 Hz).

EXAMPLE XIV

Preparation or 3-Methoxy-7H-naphtho[1,2,3-ij][2,7]naphthyridin-7-one [3-Methoxysam-pangine, 19. The general procedure described above for sampangine was followed while beginning with 4'-methoxycleistopholine (1.00 g, 3.95 mmol). Chromatography of the crude product on flash silica gel while eluting with $CHCl_3$/EtOAc (9:1) gave a yellow fraction containing the desired product plus impurities. This fraction was re-chromatographed as above to give pure 3-methoxysampangine (19) (0.06 g, 6%). An analytical sample was obtained by crystallization from CHCl$_3$: mp 225°–227° C. (lit mp 213°'215° C.); IR (KBr) 1673, 1598, 1570, 1380, 1300, 1238, 1021, 954, 750, 720, 631 cm$^{-1}$; $^1$H and $^{13}$C NMR (see Tables II and III), Anal. (exact mass, HREIMS) calcd for C$_{16}$H$_{10}$N$_2$O$_2$ m/e 262.0742, found 262.0742. The TLC, IR, $^1$H and $^{13}$C NMR data for this compound were identical in all respects to that of the authentic natural product.

EXAMPLE XV

Preparation of 4-Chloro-7H-naphtho[1,2,3-ij][2,7]naphthyridin-7-one [4-Chlorosampangine, 21]. N-Chlorosuccinimide (200 mg, 1.5 mmol) was added to a suspension of sampan-gine (232 mg, 1.0 mmol) in DMF (10 mL) and the mixture stirred at 100° C. for 24 h. The reaction was then poured onto H$_2$O (100 mL) and the solids isolated by filtration. The crude product was purified by column chromatography eluting with CHCl$_3$/EtOAc (9:1) to give 4-chlorosampangine (21) (142 mg, 53%). Crystallization from EtOAc provided an analytical sample: mp 262°–263° C.; IR (KBr) 1670, 1590, 1410, 1315, 1278, 1240, 1230, 1000, 790, 758, 725, 610 cm$^1$; $^1$H NMR (CDCl$_3$) δ7.68 (ddd, 1 H, J=7.6, 7.6, 1.4 Hz), 7.81 (ddd, 1 H, J= 7.6, 7.6, 1.4 Hz), 7.95 (d, 1 H, J=5.9 Hz), 8.41 (dd, 1 H, J=7.6, 1.4 Hz), 8.76 (dd, 1 H, J=7.6, 1.4 Hz), 8.93 (d, 1H,J=5.9 Hz), 9.09 (s, 1H); $^{13}$C NMR (CDCl$_3$) 115.7 (1), 120.0 (0), 125.6 (1), 128.5 (1), 131.7 (1), 132.0 (0), 132.2 (0), 134.8 (1), 135.0 (0), 136.9 (0), 146.0 (0), 147.2 (1), 148.2 (1), 151.5 (0), 181.2 (0) ppm; Anal. calcd for C$_{15}$H$_7$ClN$_2$O: C 67.56, H 2.65, N 10.50; found C 67.63, H 2.52, N 10.54.

EXAMPLE XVI

Preparation of 4-Azido-7H-naphtho[1,2,3-ij][2,7]naphthyridin-7-one (4-Azidosampangine, 22]. A solution of sodium azide (650 mg, 10.0 mmol) in H$_2$O (5 mL) was added to a suspension of 4-bromosampangine (312 mg, 1.0 mmol) in acetone (20 mL). The mixture was stirred at reflux for 1 h, the acetone evaporated, and H$_2$O (50 mL) added. The product was extracted into CHCl$_3$ (4×25 mL) and the organic layer dried (Na$_2$SO$_4$) and concentrated. Flash silica gel chromatography while eluting with CHCl$_3$/EtOAc (95:5) in a dark room gave pure 4-azidosampangine, (22) (220 mg, 80%). An analytical sample was obtained by crystallization from CHCl$_3$: mp 271°–272° C.; UV (MeOH) λmax 207 (log ε 4.59), 226 (log ε 4.60), 250 (log ε 4.55), 260 (log ε 4.56), 267 (sh, log ε 4.50), 295 (log ε 3.93), 307 (log ε 3.89), 400 (log ε 4.10), 416 (log ε 4.08); IR (KBr) 2120, 1670, 1590, 1485, 1405, 1375, 1335, 1310, 1275, 1238, 1140, 1020, 795, 760, 725, 610 cm$^{-1}$; $^1$H NMR (CDCl$_3$) δ7.71 (ddd, 1 H, J=7.7, 7.7, 1.4 Hz), 7.84 (ddd, 1 H, J=7.7, 7.7, 1.4 Hz), 7.87 (d, 1 H, J=5.8 Hz), 8.48 (dd, 1 H, J=7.7, 1.4 Hz), 8.84 (dd, 1 H, J=7.7, 1.4 Hz), 8.90 (d, 1 H, J=5.8 Hz), 8.94 (s, 1 H); $^{13}$C NMR (CDCl$_3$) 114.3 (1), 119.7 (0), 125.5 (1), 128.6 (1), 131.4 (0), 131.5 (1), 132.5 (0), 134.5 (1), 135.3 (0), 136.0 (0), 137.3 (1), 143.7 (0), 147.4 (1), 150.9 (0), 181.1 (0).

EXAMPLE XVII

Preparation of 4-Amino-7H-naphtho[1,2,3-ij][2,7]naphthyridin-7-one [4-Aminosampangine, 23], Method A. Hydrogen sulfide was bubbled through a solution containing 4-azidosampangine (160 mg, 0.58 mmol) and piperidine (2 drops) in MeOH (20 mL) that was precooled to 10° C. After 30 min, the temperature of the reaction was allowed to rise to ambient temperature, and after an additional 30 min the reaction was stopped. The solvent was evaporated and the residual solids chromatographed over silica using CHCl$_3$/MeOH (9:1) as eluant to give 4-aminosampangine (136 mg, 95%). The chromatography of 4-aminosampangine (23) is easily monitored through its fluorescent characteristics. An analytical sample was obtained by crystallization from DMSO: mp>325° C.; UV (MeOH) 207 (log ε 4.34), 252 (log ε 4.16), 269 (log ε 4.15), 348 (log ε 3.56), 461 (log ε 4.11); IR (KBr) 3300 (br) 1725, 1625, 1585, 1560, 1505, 1460, 1385, 1335, 1300, 1125, 1070, 725 cm$^{-1}$; $^1$H NMR (DMSO-d$_6$) δ7.72 (ddd, 1 H, J=7.5, 7.5, 1.3 Hz), 7.83 (ddd, 1 H, J=7.5, 7.5, 1.3 Hz), 7.95 (br s, 2 H), 8.21 (d, 1 H, J=5.9 Hz), 8.26 (dd, 1 H, J=7.5, 1.3 Hz), 8.38 (s, 1 H), 8.75 (dd, 1 H, J=7.5, 1.3 Hz), 8.81 (d, 1 H, J=5.9 Hz); $^{13}$C NMR (DMSO-d$_6$) 115.7 (1), 119.8 (0), 124.1 (0), 124.7 (1), 127.0 (1), 130.9 (1), 132.0 (1), 132.8 (0), 132.9 (0), 133.1 (1), 134.7 (0), 144.3 (1), 145.1 (0), 148.5 (0), 178.4 (0) ppm; Anal. calcd for C$_{15}$H$_9$N$_3$O.H$_2$O: C 67.92, H 4.18, N 15.83; found C 68.30, H 3.80, N 15.75.

Method B. A mixture of 4-bromosampangine (622 mg, 2.0 mmol) in acetone (40 mL) and sodium azide (1.30 g, 20.0 mmol) in H$_2$O (10 mL) was heated at reflux for 1 h. The acetone was then removed by evaporation, MeOH (40 mL) added, and the mixture transferred to a three necked flask and cooled to 10° C. Piperidine (2 drops) was added and a stream of hydrogen sulfide bubbled through the reaction. After 30 min, the temperature was allowed to rise to 23° C. and the reaction continued for an additional 30 min. The solvent was then removed evaporated and the residue chromatographed as above to give 4-aminosampangine (23) (450 mg, 91%).

Method C. A solution of 4-azidosampangine (273 mg, 1.0 mmol) in MeOH (50 mL) was heated at reflux for 7 days. Following evaporation of the solvent, the residue was chromatographed as above to give 4-aminosampangine (23) (119 mg, 48%).

We claim:

1. A method for preventing pathological conditions in mammals brought about by presence of a mycobacterial organism comprising administering to said mammals in a therapeutically-effective concentration, essentially consisting of a compound having the formula

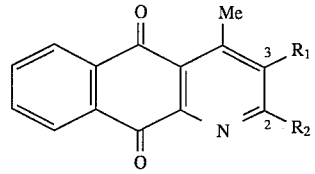

wherein R$_1$ and R$_2$ form a benzo group at the 2–3 positions in a therapeutically effective concentration and a non-toxic, pharmaceutically acceptable carrier.

* * * * *